United States Patent
Dowling, Jr.

(10) Patent No.: US 6,258,037 B1
(45) Date of Patent: Jul. 10, 2001

(54) MEASURING BLOOD PRESSURE IN NOISY ENVIRONMENTS

(75) Inventor: Neal B. Dowling, Jr., Sudbury, MA (US)

(73) Assignee: Cardiodyne Division of Luxtec Corporation, Worcester, MA (US)

( * ) Notice: Subject to any disclaimer, the term of this patent is extended or adjusted under 35 U.S.C. 154(b) by 0 days.

(21) Appl. No.: 09/344,702

(22) Filed: Jun. 25, 1999

(51) Int. Cl.[7] .................................................. A61B 5/00
(52) U.S. Cl. ........................ 600/493; 600/494; 600/490
(58) Field of Search ................................. 600/485, 490, 600/493–6, 500

(56) References Cited

U.S. PATENT DOCUMENTS

| | | |
|---|---|---|
| D. 297,260 | 8/1988 | Avoy et al. . |
| 3,651,798 | 3/1972 | Egli et al. . |
| 3,906,937 | 9/1975 | Aronson . |
| 3,906,939 | 9/1975 | Aronson . |
| 3,978,848 | 9/1976 | Yen et al. . |
| 4,058,117 | 11/1977 | Kaspari et al. . |
| 4,167,181 | 9/1979 | Lee . |
| 4,216,779 | 8/1980 | Squires et al. . |
| 4,245,648 | 1/1981 | Trimmer et al. . |
| 4,261,368 | 4/1981 | Danna et al. . |
| 4,262,674 | 4/1981 | Uemura et al. . |
| 4,295,471 | 10/1981 | Kaspari . |
| 4,308,871 | 1/1982 | Shouda et al. . |
| 4,356,827 | 11/1982 | Uemura et al. . |
| 4,408,614 | 10/1983 | Weaver et al. . |

(List continued on next page.)

FOREIGN PATENT DOCUMENTS

| | | |
|---|---|---|
| 0029349 | 5/1981 | (EP) . |
| 0256159 | 2/1988 | (EP) . |
| 0300354 | 1/1989 | (EP) . |
| 2124906 | 2/1984 | (GB) . |
| WO88/04910 | 7/1988 | (JP) . |

OTHER PUBLICATIONS

D. Abelson et al., "Bedside Measurement of Systolic and Diastolic Time Intervals Using the Stethometer," *Cardiovascular Research*, 11:270–274, 1977.

K. Bachmann et al., "Ambulatory Monitoring of Arterial Blood Pressure," *Biotelemetry Patient Monitoring*, 8:47–55, 1981.

M.W. Millar–Craig et al, "Continuous Recording of Intra–Arterial Blood Pressure During Graded Bicycle Ergometry and Stair Climbing in Essential Hypertension," *Biotelemetry Patient Monitoring*, 8:33–46, 1981.

D.L. Stoner et al., "Blood Pressure Analysis During Treadmill Stress Testing," *Journal of Clinical Engineering*, 4:369–371, Oct.–Dec. 1979.

Primary Examiner—Robert L. Nasser
(74) Attorney, Agent, or Firm—Fish & Richardson P.C.

(57) ABSTRACT

Several techniques are provided for aiding in the discrimination of detected biological signals indicative of blood pressure from detected signals not indicative of blood pressure (e.g., noise). In one technique, mixed signals which include biological signals indicative of blood pressure and noise signals not indicative of blood pressure are detected during time periods, and are evaluated over a plurality of the time periods to aid in discriminating the biological signals from the noise signals. This enhances the signal-to-noise ratio of the biological signals. In a related technique, the mixed signals are analyzed in different ways based on whether the noise level exceeds a threshold to discriminate the biological signals from the noise signals. Still another technique includes determining whether a candidate blood pressure signal should be used to measure blood pressure based on whether it exceeds a plurality of different thresholds. In another technique, a portion of the time periods in which the mixed signals are analyzed is selected based on levels of the biological signals in the mixed signals and times during a cardiac cycle intervals during which they are detected.

49 Claims, 6 Drawing Sheets

U.S. PATENT DOCUMENTS

| | | |
|---|---|---|
| 4,417,587 | 11/1983 | Ichinomiya et al. . |
| 4,461,266 | 7/1984 | Hood, Jr. et al. . |
| 4,484,584 | 11/1984 | Uemura . |
| 4,543,962 | 10/1985 | Medero et al. . |
| 4,546,775 | 10/1985 | Medero et al. . |
| 4,561,447 | 12/1985 | Kawamura et al. . |
| 4,566,463 | 1/1986 | Taniguchi et al. . |
| 4,592,365 * | 6/1986 | Georgi ................................. 600/493 |
| 4,592,366 | 6/1986 | Sainomoto et al. . |
| 4,617,937 | 10/1986 | Peel et al. . |
| 4,627,440 | 12/1986 | Ramsey, III et al. . |
| 4,638,810 | 1/1987 | Ramsey, III et al. . |
| 4,660,567 | 4/1987 | Kaneko et al. . |
| 4,745,924 | 5/1988 | Ruff . |
| 4,754,761 | 7/1988 | Ramsey, III et al. . |
| 4,777,959 | 10/1988 | Wallach et al. . |
| 4,841,980 | 6/1989 | Lee . |
| 4,867,171 | 9/1989 | Yamaguchi . |
| 4,889,132 | 12/1989 | Hutcheson et al. . |
| 4,917,098 | 4/1990 | Murase . |
| 4,938,227 | 7/1990 | Niwa et al. . |
| 4,944,305 | 7/1990 | Takatsu et al. . |
| 4,953,557 | 9/1990 | Frankenreiter et al. . |
| 4,967,756 | 11/1990 | Hewitt . |
| 4,967,757 | 11/1990 | Frankenreiter . |
| 5,014,714 | 5/1991 | Millay et al. . |
| 5,054,495 | 10/1991 | Uemura et al. . |
| 5,103,830 | 4/1992 | Shinomiya . |
| 5,392,781 * | 2/1995 | Phillips et al. ........................ 600/493 |
| 5,680,868 * | 10/1997 | Kahne et al. ......................... 600/493 |
| 5,840,036 * | 11/1998 | Voith .................................... 600/493 |
| 5,873,836 * | 2/1999 | Kahn et al. ........................... 600/493 |

* cited by examiner

| BEAT No | $P_i$ | PEAK $K_D$ | TIME | SCORE | PEAK $K_D$ | TIME $K_D$ | SCORE | CENTROID |
|---|---|---|---|---|---|---|---|---|
| | | | FROM REAL TIME CHANNEL 60a | | | FROM ACCUMULATE CHANNEL 60b | | |
| $95_1$ - 1 | $P_1$ | $K_{D1}$ | TIME $K_D$ | SCORE $K_{D1}$ | $K_{D1}$ | TIME $K_{D1}$ | SCORE $K_{D1}$ | $C_1$ |
| $95_2$ - 2 | $P_2$ | $K_{D2}$ | TIME $K_{D2}$ | SCORE $K_{D2}$ | $K_{D2}$ | TIME $K_{D2}$ | SCORE $K_{D2}$ | $C_2$ |
| . | . | . | . | . | . | . | . | . |
| $95_{n-2}$ - n-2 | $P_{n-2}$ | | | | | | | |
| $95_{n-1}$ - n-1 | $P_{n-1}$ | | | | | | | |
| $95_n$ - n | $P_n$ | $K_{Dn}$ | TIME $K_{Dn}$ | SCORE $K_{Dn}$ | $K_{Dn}$ | TIME $K_{Dn}$ | SCORE $K_{Dn}$ | $C_n$ |

94 ⎯

93 — CARDIAC GATE CENTROID

97 — MOST RECENT HEART RATE

98 — MOST RECENT DIASTOLIC

99 — AVERAGE DIASTOLIC

96 — MOST RECENT SYSTOLIC

87 — PREDICTED SYSTOLIC

MEMORY 52

FIG. 4

MEASURING BLOOD PRESSURE IN NOISY ENVIRONMENTS

BACKGROUND

This invention relates to measuring blood pressure.

Systems for measuring blood pressure are generally known. During a measurement cycle, a blood pressure cuff secured around the patient's limb is inflated to a sufficiently high pressure to cut off arterial blood flow beneath the cuff, and the cuff is incrementally deflated to allow the artery to slowly open. As the cuff is deflated, biological signals indicative of blood pressure (such as sounds, known as Korotkoff sounds, caused by the blood forcing its way through the artery) are detected by a transducer on the cuff and converted to electrical signals that are processed to determine the systolic and diastolic blood pressures. This type of measurement technique is known as auscultation.

Other blood pressure measurement techniques are known. In oscillometry, small pressure changes in an inflated cuff induced by flowing blood are detected by a transducer (disposed either on the cuff or at a remote monitor) and used as a basis for determining blood pressure. Another procedure involves using multiple transducers to detect the times of occurrence of heart pulses at different locations along the artery, and determining the blood pressure based on the pulse propagation time between the transducers.

Often it is clinically useful to measure blood pressure (by any of the techniques described above, or possibly by other techniques) during critical care periods (for example, while the patient is undergoing surgery or being treating in an intensive care unit), or as the patient exercises to, for example, monitor how blood pressure changes with variations in heart rate. But activity, by the patient or by others, during these times generates noise (i.e., signals that are not indicative of blood pressure) that may be incorrectly interpreted, resulting in inaccurate blood pressure measurement.

In some systems that measure blood pressure by auscultation, a threshold based on the level of previously received, valid Korotkoff sounds is applied to all signals produced by the transducer as a discriminant to remove noise. Some systems use two transducers that are spaced on the cuff to provide a half-period delay between the Korotkoff sounds and take the difference between the signals produced by the sensors to reinforce the Korotkoff sounds; because noise appears generally the same at each transducer, the noise level in the difference signal is reduced.

U.S. Pat. No. 5,392,781, entitled "Blood Pressure Monitoring in Noisy Environments" and assigned to the present assignee (the "'781 patent"), describes several techniques for aiding in the discrimination of blood pressure signals from noise.

SUMMARY

This invention, in general, provides enhancements to the techniques described in the '781 patent, and additional techniques used during the measurement of blood pressure for assisting the discrimination of biological signals (such as Korotkoff sounds) indicative of blood pressure from other signals not indicative of blood pressure. Examples of these other signals not indicative of blood pressure include noise generated by the movement of the subject or by the activity of others that occur in all but the quietest measurement environments and which, if not discounted, may result in erroneous measurements. The use of the techniques of this invention, separately or combined, leads to blood pressure measurements that are accurate and, equally as important, highly reliable even in high noise environments (such as those encountered with an exercising subject or when monitoring the subject in an operating room or an intensive care unit).

In one aspect of the invention, mixed signals which include biological signals indicative of blood pressure and noise signals not indicative of blood pressure are detected during time periods, and are evaluated over a plurality of the time periods to aid in discriminating the biological signals from the noise signals.

Preferred embodiments may include one or more of the following features.

The evaluation comprises assembling the mixed signals detected at corresponding times during the plurality of time periods, and analyzing the assembled mixed signals to aid in discriminating the biological signals from the noise signals. Preferably, the assembling includes accumulating the mixed signals detected at the corresponding times during the plurality of time periods.

The time periods are cardiac cycle intervals, and the accumulation is performed on samples of the mixed signals that are taken at corresponding time delays after a start of each of the cardiac cycle intervals. The start of each cardiac cycle interval is detected based on an occurrence of a timing signal that is synchronous with the cardiac cycle. Preferably, the timing signal is an R-wave signal.

Evaluating the mixed signals over multiple time periods increases the signal-to-noise ratio between the biological signals (e.g., Korotkoff sounds) and the noise signals, thereby improving the detection of the biological signals. Korotkoff sounds are rhythmic with heartbeat (that is, they occur at the same frequency as the heartbeat rhythm) while motion-induced noise (such as sounds generated by the patient's stride on a treadmill or by swinging his or her arms) generally do not occur at the heartbeat frequency. Thus, accumulating the mixed signals detected at corresponding times during the time periods reinforces the Korotkoff sound components in the mixed signals but does not reinforce the noise components in these signals. As a result, the Korotkoff sound components are emphasized with respect to noise, and thus can be detected more accurately.

The assembled mixed signals are analyzed by developing a candidate blood pressure signal based on the biological signals indicative of blood pressure in the assembled mixed signals, and determining whether the candidate blood pressure signal should be used to measure blood pressure. In general, the determination is based on whether the candidate blood pressure signal exceeds a threshold. In a preferred embodiment, the determination is based on whether the candidate blood pressure signal exceeds a plurality of combinations of different thresholds. In this approach, a score is assigned to the candidate blood pressure signal that indicates a likelihood that the candidate blood pressure signal is a valid blood pressure signal, the score being based on which thresholds are exceeded. Blood pressure is measured based on the scores of the candidate blood pressure signals.

One of the thresholds includes a history threshold. The history threshold is developed based on previously detected biological signals indicative of blood pressure in the assembled mixed signals that have exceeded the threshold. Another threshold includes a noise threshold, which is developed based on the noise signals not indicative of blood pressure in the assembled mixed signals.

In a preferred embodiment, the candidate blood pressure signal is developed from the biological signals indicative of blood pressure in the assembled mixed signals only during a selected portion of one of the time periods (e.g, cardiac cycle intervals). The selected portion is determined based on levels of the biological signals indicative of blood pressure in the assembled mixed signals and times during the cardiac cycle intervals during which they are detected.

Preferably, the mixed signals are detected with a one or more transducers on a blood pressure cuff. If a plurality of transducers are used, the mixed signals detected at corresponding times during the plurality of time periods by each transducer are assembled (e.g., by an accumulator associated with each transducer) and analyzed by processing circuitry to aid in discriminating the biological signals from the noise signals.

The assembled mixed signals from each of the transducers are combined with each other in one way to develop the candidate blood pressure signal, and are combined with each other in another way to develop the noise threshold for the candidate blood pressure signal. For example, the candidate blood pressure signal is developed by subtracting the assembled mixed signals detected by one of the transducers from the assembled mixed signals detected by another one of the transducers, which reinforces the biological signals and attenuates the noise signals. The noise threshold is developed by summing together the assembled mixed signals from the plurality of transducers, which reinforces the noise signals and attenuates the biological signals.

Another aspect of the invention features detecting mixed signals that include biological signals indicative of blood pressure and noise signals not indicative of blood pressure, determining if a noise level exceeds a threshold, and analyzing the mixed signals in a first way if the noise level does not exceed the threshold to discriminate the biological signals from the noise signals, and analyzing the mixed signals in a second, different way if the noise level exceeds the threshold to discriminate the biological signals from the noise signals.

Preferred embodiments may include one or more of the following features.

The mixed signals are detected during time periods. The first way of analyzing comprises evaluating the mixed signals in each of the time periods individually, and the second way of analyzing comprising evaluating the mixed signals over a plurality of the time periods. The second way of analyzing the signals comprises assembling the mixed signals detected at corresponding times during the time periods, and analyzing the assembled mixed signals to discriminate the biological signals from the noise signals.

The time periods are cardiac cycle intervals, and the assembling includes accumulating samples of the mixed signals that are taken at corresponding time delays after a start of each of the cardiac cycle intervals.

The noise determination is based on the detected noise signals not indicative of blood pressure in the mixed signals. The mixed signals detected during cardiac cycle intervals are analyzed to discriminate the biological signals from the noise signals, and the noise determination is based on the mixed signals detected outside of the cardiac cycle intervals.

Among other advantages, this aspect of the invention allows the blood pressure measurement to be made in real time (e.g., according to techniques described in the '781 patent) when the noise level is relatively low, while also providing more robust noise discrimination techniques (e.g., using the accumulation procedure discussed herein) in high noise environments.

In another aspect of the invention, mixed signals which include biological signals indicative of blood pressure and noise signals not indicative of blood pressure are detected, a candidate blood pressure signal is developed based on the biological signals indicative of blood pressure in the mixed signals, and a determination of whether the candidate blood pressure signal should be used to measure blood pressure is made based on whether it exceeds a plurality of combinations of different thresholds.

Preferred embodiments may include one or more of the following features.

A score is assigned to the candidate blood pressure signal that indicates a likelihood that the candidate blood pressure signal is a valid blood pressure signal. The score is based on which thresholds are exceeded. Blood pressure is measured based on the scores of the candidate blood pressure signals.

The thresholds include a history threshold, which is developed based on previously detected biological signals indicative of blood pressure in the mixed signals that have exceeded the threshold. The thresholds also include a noise threshold, which is developed based on the noise signals not indicative of blood pressure in the mixed signals.

Among other advantages, the scoring technique provides increased flexibility in deciding whether a candidate blood pressure signal should be used to measure blood pressure over binary-result techniques in which the candidate is validated only if it exceeds the history and noise thresholds. Accordingly, the signal analysis is more tolerant of ambiguous candidate blood pressure signals, and thus is less likely to produce so-called "false negative" results (in which a candidate blood pressure signal is designated as not representing a Korotkoff sound when in fact the candidate does represent a Korotkoff sound).

In another aspect, the invention features detecting mixed signals that include biological signals indicative of blood pressure and noise signals not indicative of blood pressure during time periods, selecting a portion of the time periods based on levels of the biological signals indicative of blood pressure in the mixed signals and times during a cardiac cycle intervals during which they are detected, and analyzing the biological signals indicative of blood pressure in the mixed signals only during the selected portion of the time periods to develop a candidate blood pressure signal.

Preferred embodiments may include one or more of the following features.

The portion of the time periods is selected by designating a nominal time from initiation of a cardiac cycle interval based on a weighted average of times during the cardiac cycle at which the biological signals indicative of blood pressure are detected and levels of said biological signals. The portion of the time period is started at a first time prior to the nominal time, and is ended at a second time after the nominal time. The nominal time is selected differently according to whether systolic or diastolic pressure is being measured. The first and second times are changed in accordance with changes in heart rate. A determination as to whether the candidate blood pressure signal should be used to measure blood pressure is made based on the analysis of the biological signals made in the selected porion of the time periods.

Determining the analysis portion of the time periods in this way takes advantage of the repetitive nature of the heartbeat and the relative consistency of the delay between the time the heart beats to the time that the blood pulse (which produces the Korotkoff sound) is detected. Because the arrival of the Korotkoff sound at the detector often produces the highest level in the mixed signals, determining a weighted average of the times of arrival and levels of the mixed signals is a highly accurate way of estimating the arrival of the Korotkoff sounds. Thus, basing the analysis portion of the time periods on the nominal time produced by the weighted average enhances the accuracy of the Korotkoff sound detection in the presence of noise.

Other features and advantages of the invention will become apparent from the following detailed description, and from the claims.

DRAWINGS

FIG. 4 illustrates the contents of a memory used by the noise discrimination stage.

DETAILED DESCRIPTION

Overview

Figure 1:
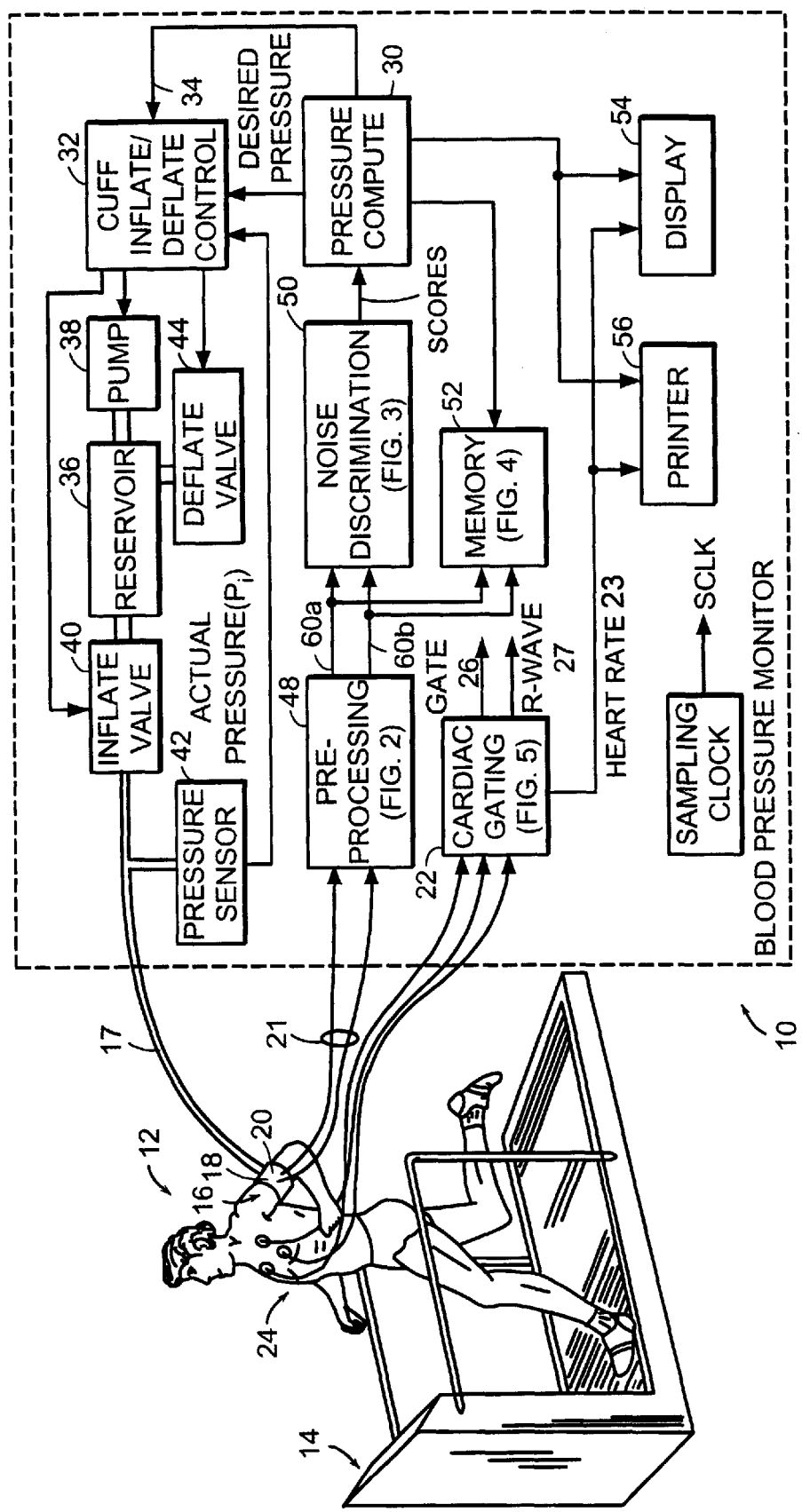
FIG. 1 shows a blood pressure monitor in use with an exercising patient.

Referring to FIG. 1, blood pressure monitor 10 includes many of the features of the blood pressure monitor described in U.S. Pat. No. 5,392,781, entitled "Blood Pressure Monitoring in Noisy Environments" ("the '781 patent"), which is assigned to the present assignee and is incorporated herein by reference. Familiarity with the description provided in the '781 patent is assumed, and thus many of such features are summarized herein. The reader is referred to the '781 for a detailed description of such features.

Blood pressure monitor 10 employs numerous techniques described in detail below for discriminating valid blood flow signals (i.e., Korotkoff sounds) from noise and other spurious signals that are typically encountered in all but the quietest environments and which, if not removed, may render the blood pressure measurement inaccurate (or, in some cases, impossible to make). The noise may be caused by the motion of patient whose blood pressure is being monitored or may be the result of activity by others, such as nearby health care providers. Thus, while patient 12 is shown exercising or undergoing a stress test on treadmill 14, the patient may alternatively be exercising in another fashion or be resting and prone and receiving care in such areas as an operating room or an intensive care unit.

Monitor 10 measures blood pressure by the auscultation technique and includes a blood pressure cuff 16 equipped with a pair of spaced, independent transducer sensing areas 18, 20 (which may comprise two portions of one transducer or a pair of transducers) each of which is connected to blood pressure monitor 10. Transducers 18, 20 are disposed under cuff 16, but other arrangements may be used instead. Cardiac gating circuitry 22 monitors the heart functions of patient 12 in a manner described in detail below with a set of cardiac electrodes 24 (only three of which are shown), and provides a gate 26 for each heart period during which signals from transducers 18, 20 are analyzed to determine the presence or absence of Korotkoff sounds. Transducer signals are also analyzed outside of the cardiac gate time to determine whether the measurement environment is excessively noisy, so that the noise discrimination process can be adjusted accordingly, as described below. Gating circuitry 22 also detects the occurrence of the R-wave in the QRS complex in the heartbeat, and generates a corresponding R-wave signal 27. A sampling clock 25 provides a 120 Hz clock signal (SCLK) used in a manner described below during noise discrimination.

Briefly, blood pressure measurement proceeds as follows. An initial blood pressure measurement is made with the patient at rest (and thus, with noise assumed to be at a minimum) to develop parameters used in the noise discrimination process, as described below. Thereafter, blood pressure measurements are made cyclically, such as every one to five minutes, under the control of a pressure compute process 30 executed by a computer (such as a microprocessor, not separately shown).

At the start of each measurement cycle, pressure compute process 30 triggers cuff controller 32 to inflate cuff 16 via hose 17 to a desired pressure 34. (Desired pressure 34 is established during the initial blood pressure measurement, and is approximately 25 mm Hg above the systolic pressure obtained during that measurement.) Cuff controller 32 fills reservoir 36 by activating pump 38 and then opens valve 40 to rapidly inflate cuff 16. Sensor 42 monitors the actual pressure ($P_i$) of cuff, digitizes the pressure measurement, and provides it to cuff controller 32. Cuff controller 32 activates pump 38 and valve 40, and if necessary deflate valve 44, to maintain $P_i$ at the desired value.

Transducers 18, 20 detect biological signals (such as Korotkoff sounds) that are indicative of blood pressure as well as signals (such as noise) that are not indicative of blood pressure, and convert these mixed signals to electrical signals. At the occurrence of each cardiac gate 26, the electrical signals from transducers 18, 20 are preprocessed (48) and applied to a noise discrimination procedure (50).

Preprocessing (48) and noise discrimination (50) are described in detail below. Suffice it here to say that they implement computer programs executed by the microprocessor to evaluate the sounds detected by transducers 18, 20 in each cardiac gate 26 (i.e., during each heartbeat period) to determine whether valid Korotkoff sounds have been received, control the deflation of cuff 16 in accordance with the evaluation, and store information about the detected sounds, the cuff pressures ($P_i$) at which they are detected, and the evaluation of the sounds in memory 52 on a heartbeat-by-heartbeat basis. Pressure compute process 30 determines candidate systolic and diastolic components of blood pressure from the stored information, and executes routines to validate the candidate systolic and diastolic pressures. Validated systolic and diastolic pressures obtained in the current measurement cycle are sent (together with present heart rate 23) to display 54 for presentation to the user. These values and other patient data are periodically sent to printer 56 to obtain a history of these functions.

Blood pressure monitor 10 provides numerous enhancements to the techniques described in the '781 patent for improving noise immunity that are described in detail below. Briefly, however, preprocessing stage 48 has been modified to include two parallel signal processing channels. The first channel is substantially the same as the preprocessing stage of the '781 patent, and processes the transducer signals in real time, so that the signals individual heartbeat periods can be evaluated. The second channel accumulates the signals produced by transducers 18, 20 over several heartbeat periods for evaluation. The accumulation reinforces rhythmic sounds (such as Korotkoff sounds) and improves signal-to-noise ratio, thereby enhancing the accurate detection of Korotkoff sounds even in extremely noisy environments. The real-time and accumulated signals from the first and second channels are both evaluated. Normally, the evaluation of the real-time signals provides the basis for determining systolic and diastolic blood pressure. But when the measurement environment is excessively noisy, the evaluation of the accumulated signals is used instead.

In addition, the determination of cardiac gate 26 has been refined to take into account not only the timing of candidate Korotkoff sounds, but also their amplitudes, so that larger amplitude signals (which are more likely to be actual Korotkoff sounds) have a greater impact on the timing of cardiac gate 26. Also, noise discrimination stage 50 has been modified to evaluate whether the detected sounds (from both the real-time channel and the accumulation channel) are valid Korotkoff sounds based on a degree of likelihood analysis, rather than in a binary way. The end result is even greater reliability in Korotkoff sound detection (e.g., fewer false positive and false negative detections) and higher blood pressure measurement accuracy, despite the presence of heavy noise.

Preprocessing

Figure 2:
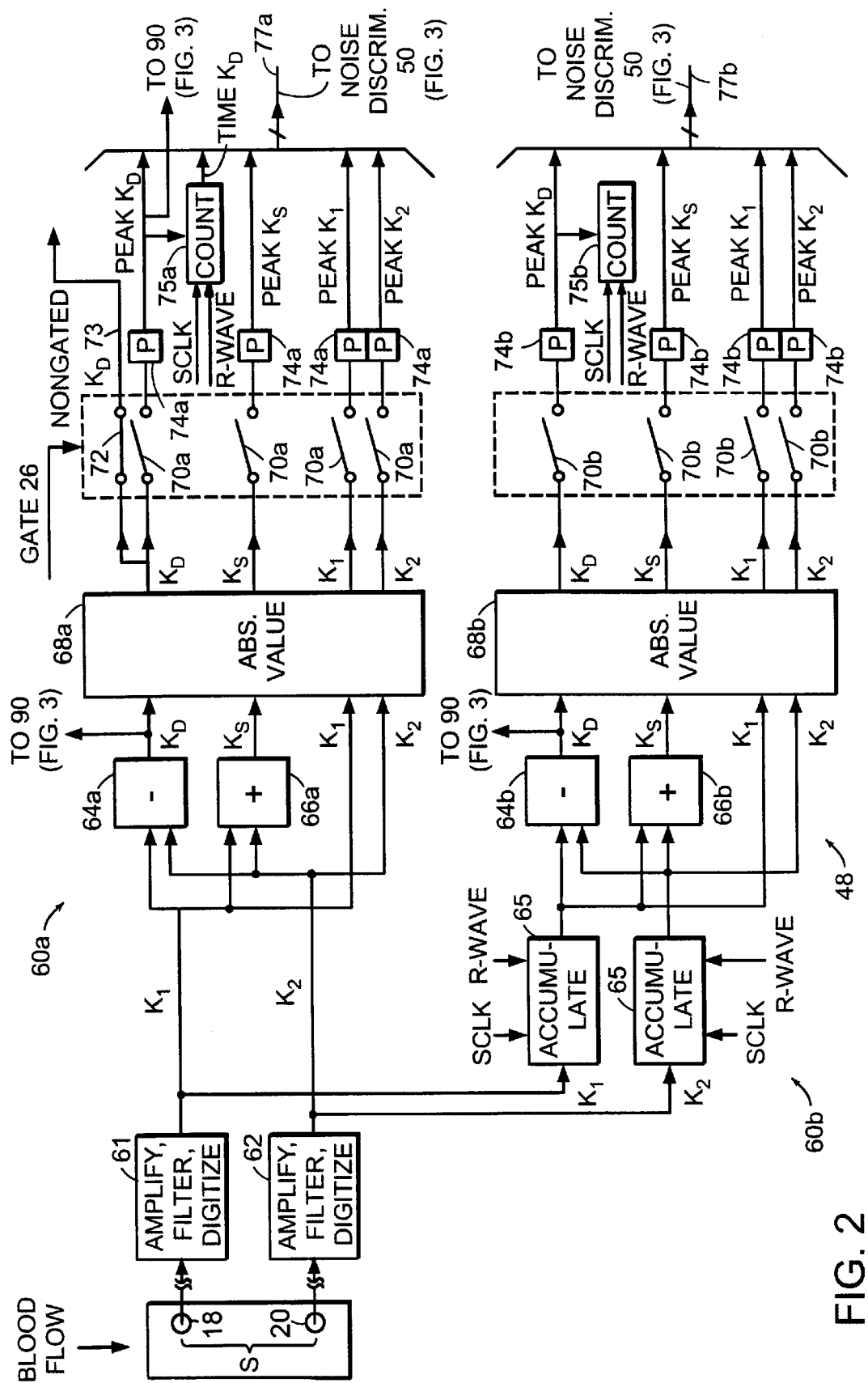
FIG. 2 shows a preprocessing stage of the blood pressure monitor of FIG. 1.

Referring to FIG. 2, preprocessing stage 48 includes a pair of processing channels 60a, 60b connected in parallel. Channel 60a is nearly identical to preprocessing stage 48 of the '781 patent, and provides signals to noise discrimination stage 50 (FIG. 1) in each heartbeat period in real-time. By "real-time" we mean that for a given heartbeat period, channel 60a produces signals associated with the sounds detected during that heartbeat period. In contrast, channel 60b includes a pair of accumulators 65 which accumulate the transducer output signals over several (e.g., six) heartbeat periods. Channel 60b also provides signals to noise discrimination stage 50 in each heartbeat period, but these signals are the result of the accumulation of the transducer signals over the six heartbeat periods.

Blood pressure cuff transducers 18, 20 are spaced on cuff 16 so that transducer 20 lies downstream (i.e., distally) of transducer 18 over an artery in the limb. While Korotkoff sounds are periodic in nature (rhythmic) and propagate at a finite speed down the length of the artery, noise is usually nonperiodic and typically appears essentially the same at different points along the artery. The spacing S between the centers of transducers 18, 20 is chosen so that transducer 20 detects Korotkoff sounds that are delayed by approximately one-half period (i.e., 180 degrees) with respect to the Korotkoff sounds detected by transducer 18, subject to patient variations. For example, spacing S is one inch. Most noise is detected substantially identically by both transducers 18, 20.

Transducers 18, 20 convert the mixed sounds that they receive (both Korotkoff sounds and noise) to electrical signals and transmit the signals via cable 21 (FIG. 1) to respective input stages 61, 62 of preprocessing stage 48. There, the signals are amplified, bandpass filtered (to remove signal frequencies that are known to be outside of the possible frequency range for Korotkoff sounds), digitized by standard analog-to-digital conversion techniques, and applied to channels 60a, 60b. The outputs of input stages 61, 62 (corresponding respectively with proximal and distal transducers 18, 20) will be identified below as $K_1$ and $K_2$, although it is understood that these signals may represent valid Korotkoff sounds, ambiguous sounds (i.e., noise) or low-level sounds that are neither blood flow sounds nor noise.

With the exception of accumulators 65, which are described below, channels 60a, 60b are substantially identical. Real time channel 60a processes transducer output signals $K_1$, $K_2$ on a heartbeat-by-heartbeat basis, while accumulate channel 60b processes transducer output signals $K_1$, $K_2$ as accumulated over six heartbeat periods.

Channels 60a, 60b include respective subtracters 64a, 64b which takes the difference between proximal transducer signal $K_1$ and distal transducer signal $K_2$ to produce a difference signal $K_D$. Transducer signals $K_1$ and $K_2$ are summed together in respective adders 66a, 66b to generate a sum signal $K_S$. Because of the one-half period delay between the Korotkoff sounds as detected by transducers 18, 20, the Korotkoff sounds are reinforced in difference signal $K_D$ and substantially canceled from the sum signal $K_S$. But because noise appears essentially the same to transducers 18, 20, the noise is reinforced in sum signal $K_S$ and substantially attenuated in difference signal $K_D$. Thus, the amplitude of difference signal $K_D$ represents that of a candidate Korotkoff sound, and sum signal $K_S$ has an amplitude used to provide a noise threshold for Korotkoff signal $K_D$.

The absolute values of sum and difference signals $K_S$, $K_D$ and the individual transducer signals $K_1$, $K_2$ are taken (68a, 68b) to provide signals that are always positive for subsequent processing. Then, the signals are applied to a set of switches 70a, 70b that are controlled by cardiac gate 26. Cardiac gate 26 closes switches 70a, 70b only during a predetermined interval of each heartbeat period during which the Korotkoff sounds are most likely to occur. This helps prevent noise detected by transducers 18, 20 between gates 26 from erroneously being interpreted as Korotkoff sounds. As discussed in detail below, one of the features of this invention is adaptively changing the timing of cardiac gate 26 in accordance with the times of arrival and amplitudes of candidate Korotkoff sounds.

Real-time channel 60a includes a second switch 72 that receives difference signal $K_D$ produced by absolute value stage 68a. The state of switch 72 is maintained opposite to that of switches 70a (i.e., switch 72 is closed only between cardiac gates 26) to provide a non-gate time $K_D$ signal 73 used (as described in detail below) to determine if the environment is unusually noisy.

During each cardiac gate 26, a set of detectors 74a, 74b determines the peak values of difference signal $K_D$, sum signal $K_S$, and individual transducer signals $K_1$ and $K_2$ in each channel 60a, 60b. The time of occurrence of peak difference signal $K_D$ in each channel 60a, 60b (time $K_D$) is also determined using counters 75a, 75b, each of which counts the number of SCLK pulses (FIG. 1) in each heartbeat period. At the start of each heartbeat period, counters 75a, 75b are reset by R-wave signal 27 (FIG. 1). Counters 75a, 75b continue counting until they receive peak difference signal $K_D$ from respective detectors 74a, 74b. Thus, the counts reached by counters 75a, 75b represent the times in the heartbeat periods at which the real-time and accumulated peak difference signals $K_D$ respectively occur (i.e., time $K_D$).

Figure 3:
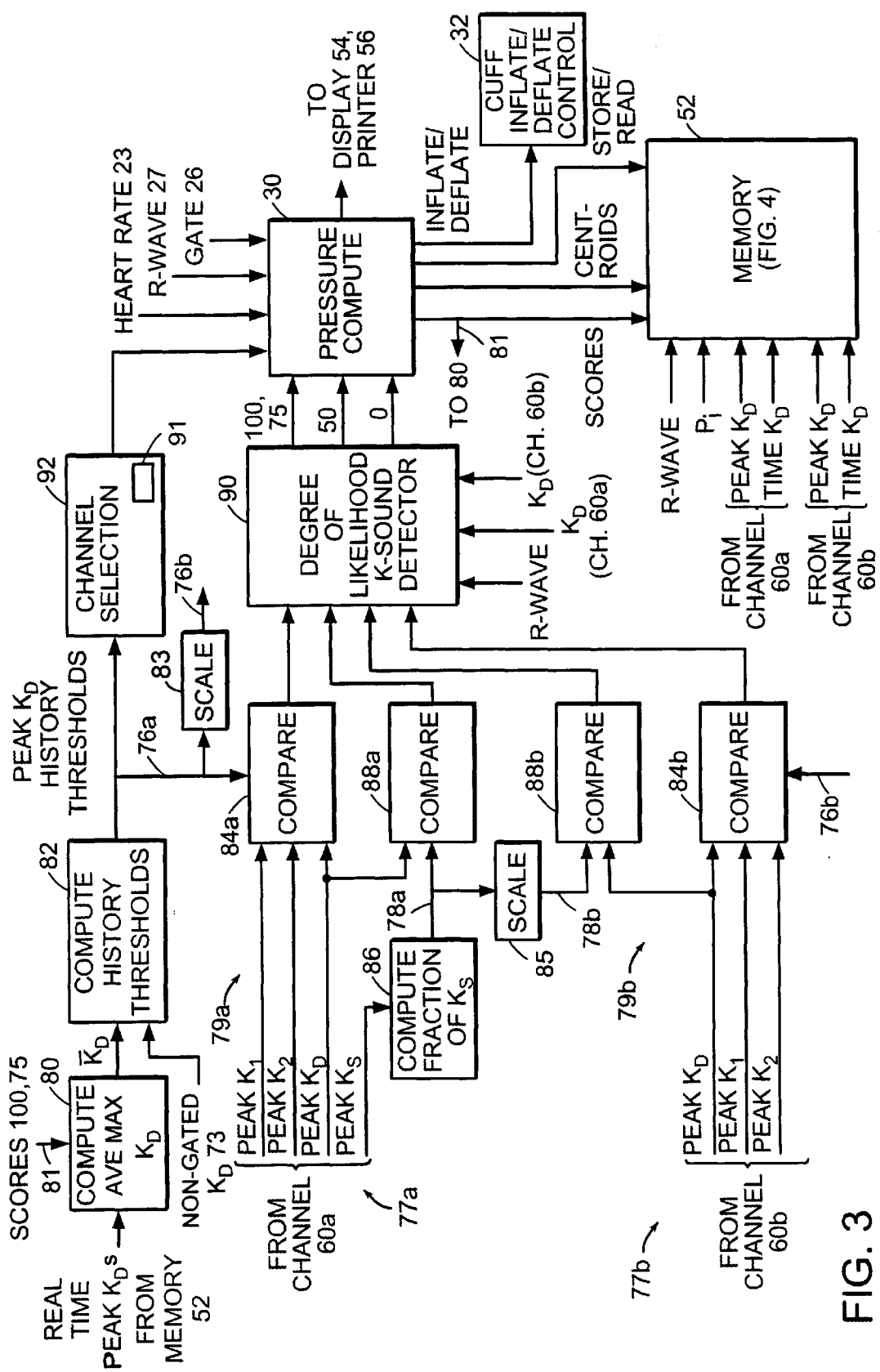
FIG. 3 shows a noise discrimination stage of the blood pressure monitor of FIG. 1.

Referring also to FIG. 3, the peak-detected and timing signals produced by channels 60a, 60b for each heartbeat period are applied as a respective set of output signals 77a, 77b to parallel evaluation sections 79a, 79b of noise discrimination stage 50. In addition, the real-time and accumulated peak $K_D$ and time $K_D$ signals produced by channels 60a and 60b during each heartbeat period are stored in memory 52. That is, for each heartbeat period, a peak $K_D$-time $K_D$ pair of signals from real time channel 60a and a peak $K_D$-time $K_D$ pair of signals from accumulate channel 60b are stored in memory 52. The purpose of storing this information is explained below.

Referring again to FIG. 2, accumulators 65 are synchronized to the occurrence of the QRS complex in the patient's heartbeat by R-wave signal 27. At the occurrence of each SCLK signal during the heartbeat, each accumulator 65 samples respective signals $K_1$ and $K_2$ and stores the samples at corresponding locations in a buffer. During each succeeding cardiac cycle (i.e., the heartbeat period between consecutive QRS complexes) each accumulator 65 adds each sample to the corresponding sample from the previous heartbeat (i.e., the sample that occurred at the same time relative to R-wave signal 27), and stores the sum in the corresponding buffer location.

Consider, for example, that N samples of either transducer output signal (which will be referred to as "K" for ease of explanation) are taken over M heartbeat periods. The N samples obtained in the initial period (period 0) can be expressed as:

$$[K_0(0), K_0(1), K_0(2) \ldots K_0(N)]$$

The N samples gathered in the succeeding periods 1–M are:

$$[K_1(0), K_1(1), K_1(2) \ldots K_1(N)] \ldots [K_M(0), K_M(1), K_M(2) \ldots K_M(N)]$$

Accordingly, the accumulated samples stored in buffer locations 0–N are:

$$\sum_{i=0}^{M} K_i(0), K_i(1), K_i(2) \ldots K_i(N)$$

or $$\left[\sum_{i=0}^{M} K_i(0), \sum_{i=0}^{M} K_i(1), \sum_{i=0}^{M} K_i(2) \ldots \sum_{i=0}^{M} K_i(N)\right]$$

Thus, it is seen that, in each accumulator 65, the samples occurring at the same time after R-wave signal 27 in each beat are added together over the M beats and the result stored in the corresponding buffer location. Each accumulator 65 thus assembles the transducer output signals detected at corresponding times during the M heartbeat periods for evaluation by noise discrimination stage 50.

Accumulators 65 assemble transducer output signals $K_1$ and $K_2$ over six heartbeat periods (i.e., M=6). In each heartbeat period, accumulators 65 apply the current accumulated values to subtracter 64b, adder 66b, and absolute value stage 68b for processing in the same way as discussed above and in the '781 patent.

Accumulators 65 perform a rolling accumulation. That is, only the $K_1$ and $K_2$ signals for the most recent six heartbeat periods are accumulated, and accumulators 65 store a running accumulation of the samples of transducer output signals $K_1$ and $K_2$ over those six heartbeat periods. After six heartbeat periods, samples of the $K_1$ and $K_2$ signals for the next (i.e., seventh) heartbeat overwrite the $K_1$ and $K_2$ signals for the first heartbeat, and samples of the $K_1$ and $K_2$ signals for heartbeat periods 2–7 are accumulated (summed). Samples of the $K_1$ and $K_2$ signals for the eighth heartbeat overwrite the $K_1$ and $K_2$ signals for the second heartbeat, and the samples of the $K_1$ and $K_2$ signals for heartbeat periods 3–8 are accumulated (summed). The accumulation proceeds in the same manner in accumulators 65 for all subsequent heartbeat periods.

The benefits of accumulating transducer output signals $K_1$ and $K_2$ in this way will be appreciated by considering the physiology of Korotkoff sounds and the typical sources of noise in the measurement environment. First, Korotkoff sounds are rhythmic, that is, they occur at regular intervals, while motion-induced noise (such as sounds generated by the patient's stride on a treadmill or by swinging his or her arms) is not. Thus, sampling transducer output signals $K_1$ and $K_2$ during several heartbeats and accumulating samples which occur at the same time after a reference point (e.g., the R-wave of each heartbeat) will reinforce the Korotkoff sound components in transducer output signals $K_1$ and $K_2$, but will not reinforce the noise components in these signals. As a result, the accumulated samples stored in accumulators 65—and hence the accumulated values of peak $K_D$, peak $K_S$, peak $K_1$, and peak $K_2$ applied to noise discrimination stage 50—will tend to have an improved signal-to-noise ratio compared with their non-accumulated counterparts in channel 60a.

Noise Discrimination

FIG. 3 is a detailed functional block diagram of the preferred noise discrimination stage (50). As discussed above, noise discrimination stage 50 includes sections 79a, 79b for evaluating signals 77a, 77b from real-time channel 60a and accumulate channel 60b in parallel for each heartbeat period.

As with the noise discrimination stage of the '781 paten, section 79a compares the peak values of the real-time $K_D$, $K_1$ and $K_2$ signals with history thresholds 76a, and compares the real-time peak $K_D$ signal with a noise threshold 78a to evaluate the validity of the candidate Korotkoff sounds. Section 79b also evaluates the validity of candidate Korotkoff sounds by likewise comparing the peak values of the accumulated $K_D$, $K_S$, $K_1$ and $K_2$ signals with history and noise thresholds 76b, 78b (which are derived from the thresholds 78a, 78b used in real-time evaluation channel 79a, as discussed below).

The thresholding tests of the '781 patent are binary (i.e., the history threshold comparisons and the noise threshold comparisons all had to be satisfied in order for a candidate Korotkoff sound to be considered valid). In contrast, the present noise discrimination stage 50 includes a degree of likelihood Korotkoff sound detector 90 which assigns a score (100, 75, 50, or 0) to candidate Korotkoff sounds from real-time channel 60a and accumulate channel 60b (i.e., the real-time and accumulated peak $K_D$ signals applied during a cardiac gate 26 by preprocessing stage 22) based on which combinations of threshold comparisons are satisfied. Pressure compute process 30 evaluates the scores of the candidate Korotkoff sounds to determine their validity, and stores the scores in memory 52 with the associated peak $K_D$ signals, as discussed below.

In real-time evaluation stage 79a, the history threshold comparisons are made by compare block 84, which compares the amplitudes of the real-time candidate Korotkoff sound (peak $K_D$) and the real-time individual transducer signals (peak $K_1$ and peak $K_2$) to thresholds 76a ($K_D$ thresholds) that are based on the history of previously received, valid Korotkoff sounds. For a given measurement cycle, history thresholds 76a are derived based on the average maximum real-time $K_D$ signals ($\overline{K_D}$) obtained in the previous measurement cycle. (A preset value representative of the amplitude of a normal Korotkoff sound is used as the average maximum amplitude ($\overline{K_D}$) for the initial measurement cycle; the preset value is updated after the initial cycle as described below.)

Block 80 derives the average maximum amplitude ($\overline{K_D}$) of the real-time peak $K_D$ signals as follows. At the end of a measurement cycle, block 80 analyzes the real-time peak $K_D$ signals stored in memory 52 that have scores of 75 or 100 (which, as described below, means that such signals are likely to represent valid Korotkoff sounds). Block 80 selects the four highest amplitude peak $K_D$ signals that have scores of 75 or 100. Block 80 discards the highest amplitude peak $K_D$ signal, and determines the average amplitude of the other three peak $K_D$ signals. This average is designated as the average maximum amplitude ($\overline{K_D}$) to be used in the next measurement cycle.

As described in the '781 patent, block 82a derives history thresholds 76a by computing fractions of the average maximum amplitude $\overline{K_D}$, and block 84a performs a comparison between the real-time peak $K_D$, $K_1$, and $K_2$ signals in each gate 26 and history thresholds 76a. The levels of history thresholds 76a are the same as in the '781 patent. That is, the history threshold 76a with which real-time peak $K_D$ is compared is 25% of the average maximum amplitude $\overline{K_D}$. Because Korotkoff sounds are reinforced in $K_D$, the amplitude of $K_D$ should exceed that of $K_1$, and $K_2$, and consequently a lower history threshold 76a is used for the real-time $K_1$ and $K_2$ signals. The history threshold with which $K_1$ and $K_2$ are compared is ¼ of the history threshold used for $K_D$ (i.e., 6.25% of the average maximum amplitude $\overline{K_D}$).

Compare block 84a indicates to degree of likelihood detector 90 whether the applicable history thresholds 76a are or are not exceeded in each comparison. The operation of degree of likelihood detector 90 in response to this indication is discussed below.

Compare block 88 compares the amplitude of the candidate Korotkoff sound from real-time channel 60a (peak $K_D$) with a noise threshold 78a derived in block 86 from the sum signal (i.e., peak $K_S$) from real-time channel 60a, as described in the '781 patent. Noise threshold 78a changes on a cardiac gate-by-gate basis. That is, noise threshold 78a used for a candidate Korotkoff sound detected in a given cardiac gate 26 is based on the real-time sum signal (i.e., peak $K_S$) applied to block 86 from channel 60a during that gate 26. Block 86 computes noise threshold 78a in the same way as that described in the '781 patent. That is, noise threshold 78a is computed to be 83% of the real-time peak $K_S$ for heart rates less than 120 beats per minute; for greater heart rates, 100% of $K_S$ is used.

Compare block 88a indicates to degree of likelihood detector 90 whether noise threshold 78a is or is not exceeded by the real-time candidate Korotkoff sound (i.e., peak $K_D$) The operation of degree of likelihood detector 90 in response to this indication is discussed below.

The techniques described in the '781 patent for adaptively adjusting history and noise thresholds 76a, 78a according to noise level (see FIG. 4 and col. 13, line 59—col. 15, line 27 of the '781 patent) are used in blood pressure monitor 10. Reference is made to the above-identified passages of the '781 patent for details, but briefly, thresholds 76a, 78a are increased during a measurement cycle if the measurement environment is excessively noisy, as indicated by comparing the amplitude of difference signal $K_D$ outside of each cardiac gate (i.e., non-gate time $K_D$ signal 73) with $K_D$ history threshold 76a. Thresholds 76a, 78a are decreased in the same manner described in the '781 patent when the noise level subsides.

Compare block 84b in evaluation section 79b compares the accumulated peak $K_D$, peak $K_1$, and peak $K_2$ signals from channel 60b with history thresholds 76b that are derived by scaling real-time history thresholds 76a in block 83. Specifically, block 83 scales history thresholds 76a as a function of the number of heartbeats over which the signals are accumulated. This is done because the improvement in signal-to-noise ratio obtained by accumulating (or averaging) the $K_1$ and $K_2$ signals grows as the square root of the number of beats averaged (or accumulated). Thus, in this embodiment, because signals are accumulated over six heartbeat periods, block 83 increases each history threshold 76a by $\sqrt{6}$ to produce the corresponding history thresholds 76b.

For the same reasons, block 85 scales noise threshold 78a by $\sqrt{6}$ to produce noise threshold 78b for use in evaluation section 79b. Block 88b compares the accumulated peak $K_D$ signals from channel 60b with noise threshold 78b.

Compare blocks 84b, 88b indicate to degree of likelihood detector 90 whether history and thresholds 76b, 78b are or are not exceeded by the accumulated peak signals from channel 60b. The operation of degree of likelihood detector 90 in response to this indication is discussed below.

Degree of likelihood detector 90 evaluates the results of each comparison block 84a, 84b, 88a, 88b for each cardiac gate, and assigns scores to the real-time and accumulated candidate Korotkoff sounds (i.e., the peak $K_D$ signals from channels 60a, 60b) according to which combination of the comparisons is successful. Candidate Korotkoff sounds for which all history thresholds 76a or 76b and noise threshold 78a or 78b are exceeded are assigned a score of 100, which signifies that the candidate is highly likely to be a Korotkoff sound. If less than all of the thresholds are exceeded, degree of likelihood detector 90 evaluates other combinations of the comparison results and the behavior of the peak $K_D$ signal during the current heartbeat (i.e., cardiac gate), and based on this evaluation assigns a lower score to indicate the lower probability that the candidate is a Korotkoff sound.

More specifically, degree of likelihood detector 90 determines if one or more of the following conditions are satisfied for candidate Korotkoff sounds (from either real-time channel 60a or accumulate channel 60b) that do not score 100:

1. whether peak $K_D$ exceeds either the history threshold or the noise threshold;
2. whether peak $K_D$ is greater than 2.5 times the standard deviation of peak $K_D$ during the current heartbeat period;
3. whether peak $K_1$ and peak $K_2$ both exceed their history thresholds. Degree of likelihood detector 90 determines the standard deviation of peak $K_D$ based on the $K_D$ signals applied to detector 90 from subtracters 64a, 64b (FIG. 2) during the current heartbeat period (the start of which is indicated by R-wave signal 27). Thus, for real-time peak $K_D$ signals, the standard deviation of the real time $K_D$ signal as produced by subtracter 64 in channel 60a is determined; in contrast, the standard deviation of the accumulated $K_D$ signal as produced by subtracter 64 in channel 60b is determined for the evaluation of the accumulated peak $K_D$ signals.

If conditions 1–3 are all satisfied for a given candidate (i.e., peak $K_D$), degree of likelihood detector 90 determines that the candidate is quite likely to be a Korotkoff sound, and assigns a score of 75 to it. Candidate Korotkoff sounds that receive a score of 75 or 100 are equivalent to the "valid" Korotkoff sounds described in the '781 patent.

If condition 1 is not satisfied, but conditions 2 and 3 are satisfied, degree of likelihood detector 9 determines that the candidate is even less likely to be a Korotkoff sound, and assigns it a score of 50. Such Korotkoff sounds are "ambiguous," as described in the '781 patent. If either or both of conditions 2 and 3 are not satisfied (even if condition 1 is met), the candidate is highly unlikely to be a Korotkoff sound, and it is assigned a score of 0 by degree of likelihood detector 90. This is the same as a "no event," as described in the '781 patent.

Referring also to FIG. 4, pressure compute process 30 stores information from real-time channel 60a and accumulate channel 60*b* on a heartbeat-by-heartbeat basis as records (referred to generally as 95) in a table 94 in memory 52. More specifically, for each of the patient's heartbeats (beat no.) during a blood pressure measurement cycle, pressure compute process 30 stores a record 95 in table 94 that is indexed by beat number. Thus, record $95_1$ corresponds to heartbeat #1 in the measurement cycle, record $95_2$ corresponds to heartbeat #2, and so forth, through record $95_n$ for the nth heartbeat. The record $95_i$ for each beat (i.e., beat i) includes the cuff pressure $P_i$ associated with that beat, the peak $K_D$ and time $K_D$ signals obtained from real-time and accumulate channels 60*a*, 60*b* during that beat, and the scores of those real-time and accumulated peak $K_D$ signals assigned by detector 90.

Process 30 also stores other information (not shown) relevant to the scoring of data in each heartbeat period in records $95_i$. For example, process 30 stores history thresholds 76*a*, 76*b*, noise thresholds 78*a*, 78*b*, and non-gated $K_D$ signals 73. In addition, a cardiac gate centroid ($C_i$) is stored in each record $95_i$ for purposes to be discussed.

Pressure compute process 30 evaluates the scores of candidate Korotkoff sounds stored in table records 95 to determine when the systolic and diastolic pressures have been found, and to control deflation of cuff 16. The evaluation process is described in detail below, but in summary is as follows. In each heartbeat period (i.e., beat i), process 30: (1) determines which peak $K_D$ score associated with that beat (i.e., the score derived from either real-time channel 60*a* or the score from accumulate channel 60*b*) to evaluate, and decides, based on that score, whether to continue deflating cuff 16 or to hold cuff 16 at its present level for another heartbeat period; (2) evaluates that peak $K_D$ score and the peak $K_D$ scores associated with the previous two heartbeats (i.e., beats i–1 and i–2) from the same channel; (3) determines whether the evaluated scores satisfy criterion (described below) for candidate systolic or diastolic blood pressure; and (4), if so, determines the systolic or diastolic pressure from the cuff pressures ($P_i$) (from those and other heartbeat periods) stored in table 94.

Process 30 determines whether to use the real-time or accumulated scores based on the output of channel selection block 92 (FIG. 2), which indicates on the noisiness of the measurement environment. Block 92 analyzes the noise level during each heartbeat period by comparing history threshold 76*a* used for the real time peak $K_D$ signal to a reference value representing a predetermined, threshold noise level, which is stored in buffer 91 at the beginning of each measurement cycle. As long as block 92 indicates that the peak $K_D$ history threshold does not equal or exceed the reference value by a predetermined amount (e.g., by a multiple of three), process 30 makes the evaluation for that heartbeat period using the peak $K_D$ scores derived from real time channel 60*a*. In contrast, if block 92 indicates that peak $K_D$ history threshold 76*a* is equal to or greater than three times the reference value, the measurement environment is excessively noisy, and process 30 makes the evaluation for that heartbeat period using the peak $K_D$ scores derived from accumulate channel 60*b*.

For the initial measurement cycle, the reference level stored in buffer 91 is set at a relatively low value indicative of the lower limit of audibility. The initial measurement cycle is performed when the patient is resting, and thus noise level is at a minimum and the risk that peak $K_D$ history threshold 76*a* will equal or exceed three times even this low reference value is small. At the beginning of the next measurement cycle, a new peak $K_D$ history threshold 76*a* is determined by block 82 based on the average maximum $K_D$ value determined by block 80 (as discussed above). The new peak $K_D$ history threshold 76*a* is loaded into buffer 91, and becomes the reference level for the upcoming blood pressure measurement cycle.

During a measurement cycle, block 82 adjusts (increases or decreases) peak $K_D$ history threshold 76*a* based on the level of non-gated $K_D$ signal 73 (as summarized above and discussed in detail in the '781 patent). Block 92 compares peak $K_D$ history threshold 76*a* to the reference level stored in buffer 91 during each heartbeat period. As long as block 92 indicates that peak $K_D$ history threshold 76*a* is less than three times the reference level, process 30 uses the scores derived from real-time channel 60*a* in the evaluation. If, however, block 92 indicates that peak $K_D$ history threshold 76*a* equals or exceeds three times the reference level, process 30 uses the scores derived from accumulate channel 60*b* instead. At the end of the measurement cycle, the reference level stored in buffer 91 is updated based as described above.

If a candidate Korotkoff sound (as represented by a peak $K_D$ signal) being evaluated in a given heartbeat period has a score of either 100 or 75, it is highly likely that it represents a Korotkoff sound. In contrast, if the peak $K_D$ signal being evaluated has a score of 0, it is likely to correspond to no event at all in the blood pressure measurement. In either case, pressure compute process 30 responds by triggering cuff controller 32 (FIG. 1) to continue the measurement by incrementally deflating cuff 16, and transducer signals obtained in the next heartbeat are measured at the new pressure $P_i$ upon the occurrence of the next cardiac gate 26.

On the other hand, if the candidate Korotkoff sound being evaluated has a score of 50, the candidate is ambiguous and more likely than not is noise. The blood pressure measurement at the current pressure $P_i$ is thus ambiguous, and pressure compute process 30 directs controller 32 to hold cuff pressure $P_i$ at its current, level. Measurement of the signals produced by transducers 18, 20 and noise discrimination 50 are repeated for this pressure during the next cardiac gate 26. If the noise level has abated by this time (as often occurs) then the result of noise discrimination 50 will be either a "no event" (score=0) or a Korotkoff sound that is likely to be valid (score=100 or 75); if so, pressure compute process 30 proceeds as discussed above.

At times, the noise level will not have abated by the time that the next cardiac gate occurs, and the candidate Korotkoff sound obtained during that gate and stored in table 94 will again have a score of 50. In that case, pressure compute process 30 again causes cuff controller 32 to maintain the pressure of cuff 16 at its current level, and the measurement and noise discrimination steps are repeated at the next cardiac gate. If ambiguous sounds appear during a predetermined number of (such as four) consecutive cardiac gates 26, pressure compute process 30 incrementally deflates cuff 16 and measures and analyzes signals from transducers 18, 20 at the new pressure $P_i$ during the next cardiac gate 26. This prevents the blood pressure measurement from being suspended indefinitely during prolonged periods of high noise.

Pressure compute process 30 analyzes the scores stored in records 95 of table 94 on a heartbeat-by-heartbeat basis as follows to determine systolic and diastolic blood pressure.

During systolic measurement, pressure compute process 30 determines whether the sum of the evaluated scores for three consecutive heartbeat periods (i.e., three consecutive cardiac gates 26) is greater than 150. If so, process 30 determines that the systolic pressure has been found, and proceeds to analyze those scores and the scores associated with previous beats to identify a candidate systolic pressure. Process 30 analyzes the pressures $P_i$ stored with the three scores in records 95, and identifies the highest of these pressures ($P_k$) for which the associated score is either 75 or 100. Process 30 then identifies the lowest pressure ($P_1$) stored in table 94 that is greater than pressure $P_k$ and that has an associated score of 0 or 50. Process 30 calculates the candidate systolic pressure as the average of pressures $P_k$ and $P_1$.

For example, consider the following pressures and scores stored in table records 95 are (assume that pressure decreases from $P_0$–$P_4$):

| Pressure | Score |
|----------|-------|
| $P_0$ | 50 |
| $P_1$ | 0 |
| $P_2$ | 50 |
| $P_3$ | 75 |
| $P_4$ | 100 |

Pressures $P_0$–$P_2$ and pressures $P_1$–$P_3$ do not meet the requirement of having scores with a sum greater than 150. Thus, they do not trigger an indication that systolic pressure has been found. But the scores associated with pressures $P_2$–$P_4$ have a sum that exceeds 150, and thus pressure compute process 30 determines that systolic pressure has been found based on these pressures. Process 30 designates pressure $P_2$ as pressure $P_k$ in the above algorithm, because pressure $P_2$ is the highest of pressures $P_2$–$P_4$ associated with a score of 75 or 100. Process determines that pressure $P_1$ is pressure $P_1$ in the above algorithm, because pressure $P_1$ is the lowest pressure above $P_2$ with a score of 50 or 100. Thus, process 30 designates the average of pressure $P_1$ and $P_2$ as a candidate for the systolic pressure.

The procedure works in the same manner regardless of whether the evaluated scores are derived from real-time channel 60a or accumulate channel 60b. However, if the scores are from accumulate channel 60b, process requires that at least six records $95_i$ have been entered in table 94 (FIG. 4) before starting to evaluate the scores for systolic pressure. This is done to ensure that the accumulate buffers are completely filled.

Pressure compute process 30 does not accept the candidate systolic pressure unless it is at least 20 mm Hg below the initial cuff inflation pressure. If the candidate systolic pressure is rejected, cuff 16 is reinflated, and the measurement procedure is repeated one more time, starting at a new, higher initial cuff inflation pressure. The candidate systolic pressure obtained during the remeasurement is accepted. If, during a given measurement cycle, a candidate systolic pressure changes in a direction opposite to the direction in which the heart rate has changed since the previous measurement cycle (e.g., systolic pressure decreases despite an increase in heart rate), the candidate systolic pressure is not rejected, but a warning that patient 12 may be in distress is shown on display 54 (FIG. 1).

If the candidate systolic pressure is accepted, pressure compute process 30 stores it as the most recent systolic pressure in location 96 of memory 52, and stores the heart rate at which the systolic pressure was obtained (as explained below) in memory location 97. The systolic pressure is also sent to display 54 and printer 56. Cuff controller 32 rapidly deflates cuff 16 to a pressure that is 15 mm Hg above the average diastolic pressure 99 (i.e., as determined in previous measurement cycles).

Process 30 uses the most recent systolic pressure and heart rate to predict the systolic pressure that will be obtained in the next measurement cycle. Specifically, process 30 establishes the predicted systolic pressure 95 as the most recent systolic pressure 96 plus (or minus) the change in heart rate from that of the previous measurement cycle. Process 30 stores the predicted systolic pressure in memory location 87. (Pressure compute process 30 sets the initial cuff inflation pressure during the next blood pressure measurement cycle at 20 mm Hg above the predicted systolic pressure stored in location 87.)

Noise discrimination 50 operates during the measurement of the diastolic pressure in a similar manner as described above. If a peak $K_D$ receives a score of 100, 75, or 0, cuff 16 is incrementally deflated. If an ambiguous sound (score= 50) is detected, cuff pressure is maintained and the analysis of the transducer signals is repeated for up to four consecutive cardiac gates in an attempt to obtain a valid measurement (i.e., Korotkoff sound or "no event") for that pressure, as discussed above.

Measurement continues until process 30 determines that the sum of the scores stored in table 94 for three consecutive beats is less than 50 (i.e., there must be three consecutive cardiac gate periods having peak $K_D$ scores of 0). This signifies that diastolic pressure has been found, and process 30 proceeds to analyze those scores and the scores associated with previous beats to identify a candidate diastolic pressure. This is done as follows. Process 30 examines the peak $K_D$ values stored in table 94 in reverse order (i.e., in order of ascending pressure $P_i$). Process 30 identifies the highest pressure ($P_k$) associated with the three consecutive 0 scores. Then, process identifies the lowest pressure ($P_1$) above $P_k$ that has a score of 50 or higher. Process 30 computes the candidate diastolic pressure as the average of pressures $P_1$ and $P_k$.

For example, consider the following pressures and scores stored in table records 95 are (assume that pressure decreases from $P_0$–$P_5$):

| Pressure | Score |
|----------|-------|
| $P_0$ | 100 |
| $P_1$ | 75 |
| $P_2$ | 50 |
| $P_3$ | 0 |
| $P_4$ | 0 |
| $P_5$ | 0 |

Pressures $P_3$–$P_5$ are the first three consecutive pressures associated with scores of 0, and thus process 30 determines that a candidate diastolic pressure has been found based on these pressures. Next, process designates pressure $P_3$ as $P_k$ in the above algorithm, because pressure $P_3$ is this highest pressure associated with the 0 scores. Process 30 designates pressure $P_1$ as $P_1$ in the above algorithm, because pressure $P_1$ is the lowest pressure above $P_k$ having a score of 75 or 100. Thus, process 30 designates the average of pressure $P_1$ and $P_3$ as a candidate for the diastolic pressure.

Unlike the procedure discussed in the '781 patent, pressure compute process accepts the candidate diastolic pressure without further validation (although the additional validation steps performed in the '781 patent may be used, if desired). Pressure compute process 30 sends the diastolic pressure to display 54 and printer 56 for presentation to the user. Pressure compute process 30 stores the diastolic pressure as the most recent diastolic pressure in memory location 98. Pressure compute process 30 also uses the most recent diastolic pressure to update the average of the diastolic pressures measured in previous measurement cycles (and stored in memory location 99). This is done by adding the previous average to the diastolic pressure obtained in the current measurement cycle and dividing the result by two. The new average is stored in memory location 99. Cuff 16 is then fully deflated.

The entire systolic and diastolic measurement and validation procedure is repeated in the next, regularly scheduled measurement cycle. Table 94 is cleared at the start of the next measurement cycle, but the stored values for predicted systolic pressure 87, most recent systolic pressure 96, most recent heart rate 97, most recent diastolic pressure 98, and average diastolic pressure 99 are maintained and used during the next measurement cycle.

Cardiac Gating

Figure 5:
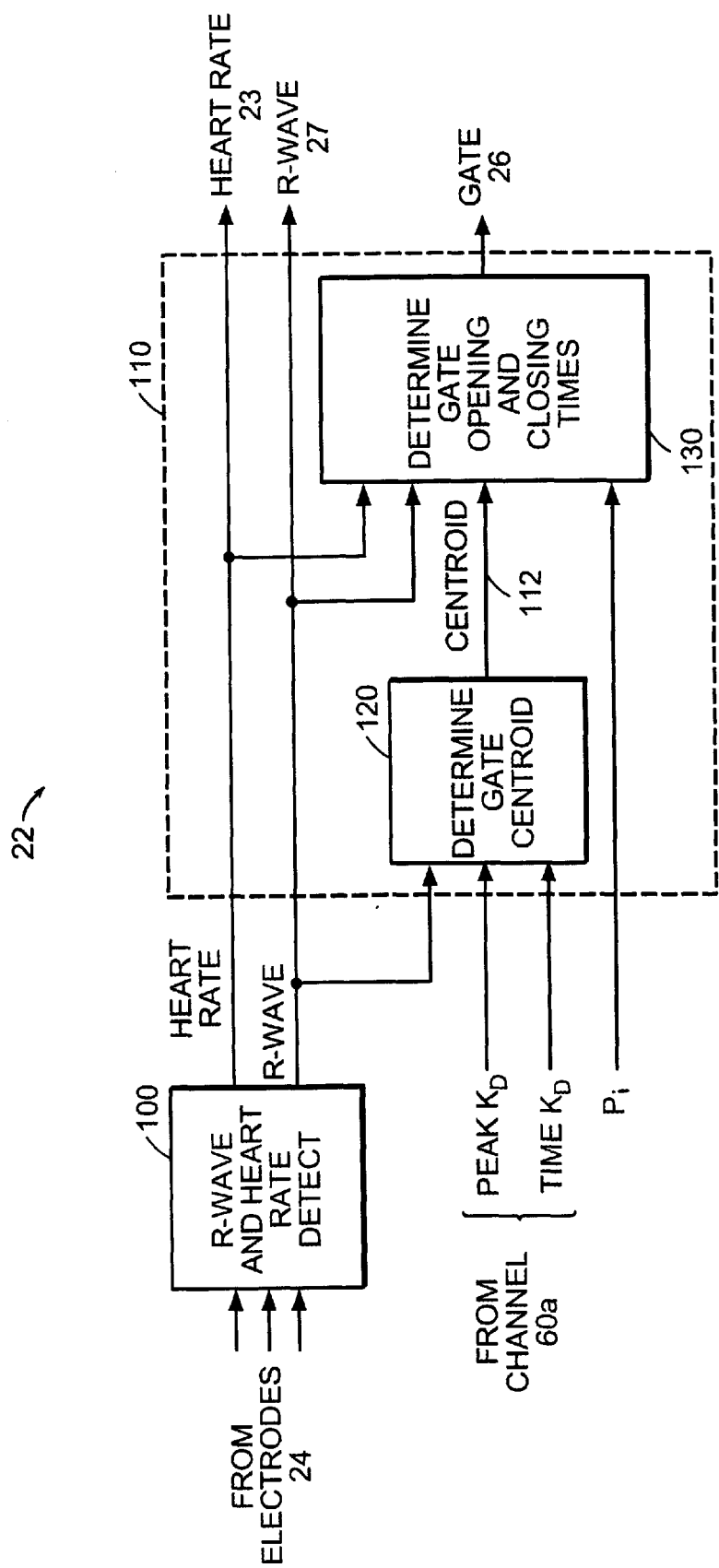
FIG. 5 shows a stage of the blood pressure monitor of FIG. 1 that issues cardiac gate signals.

Referring to FIG. 5, cardiac gating circuitry 22 is identical to that of the '781 patent in the way in which the R-wave and the heart rate (and its inverse, the heart period) are detected. Thus, all of this functionality (shown in detail in FIG. 5 of the '781 patent) is represented by block 100 of the present FIG. 5. But we note here that heart rate 23 is determined throughout the blood pressure measurement, and is stored in memory location 97 (FIG. 4) for use as described below. (It should also be noted that counter 156 of the '781 patent, which determines the time delay between the R-wave and the peak $K_D$ signal is represented by counter 75 in real-time channel 60a of the present FIG. 2.) The manner in which cardiac gate 26 is determined (block 110), however, differs substantially from the '781 patent.

Gate determination 110 is a two step procedure. First, the centroid 112 (i.e., the nominal time at which cardiac gate 26 is to occur) is determined (block 120) as a weighted average of the times of detection of the candidate Korotkoff sounds during the heartbeat period (i.e., the $K_D$ times weighted according to the amplitudes of the corresponding peak $K_D$ signals). The centroid 112 determined for each heartbeat period (i.e., $C_i$) is stored in corresponding record $95_i$ in table 94 (FIG. 4). The opening and closing times (i.e., the duration) of cardiac gate 26 are then determined (block 130) as +/− tolerances around centroid 112.

Centroid determination block 120 receives R-wave signal 27 from upstream block 100 and the peak $K_D$/time $K_D$ signal pairs produced by real-time channel 60a (FIG. 2). Determining the timing and duration of cardiac gate 26 based on centroid 112 of gate 26 takes advantage of the fact that, for a given pressure $P_i$, Korotkoff sounds typically arrive at cuff 16 with the same relative delay after the time of the heart beat (i.e., after the R-wave), for every heart beat. Centroid determination 120 calculates this delay time based not only on the times of detection (time $K_D$) of each candidate Korotkoff sound (peak $K_D$), but also on the amplitudes of the candidate Korotkoff sounds (i.e., the amplitudes of the peak $K_D$ signals), according to the following equation:

$$centriod = \frac{\sum_i [peak\ K_{Di} \times time\ K_{Di}]}{\sum_i [peak\ K_{Di}]}$$

In the above equation, peak $K_{Di}$ is the largest $K_D$ signal obtained by preprocessing stage 48 (FIG. 2) during the with heartbeat, and time $K_{Di}$ is the time determined by preprocessing stage 48 for that $K_D$ signal (i.e., the time delay between the occurrence of R-wave signal 27 for the ith beat and the peak $K_{Di}$ signal). Thus, it is seen that larger peak $K_D$ signals (i.e., candidate Korotkoff sounds) carry more weight than smaller ones in the centroid determination.

The last value of centroid 112 calculated during a given measurement cycle (i.e., $C_n$, FIG. 4) is stored in memory location 93 (FIG. 4) and is used as the centroid 112 for the next measurement cycle. Put another way, centroid 112 initially used in a given measurement cycle is determined based on the centroid calculations made throughout the prior measurement cycle.

During each measurement cycle, the gate centroid 112 is read from memory location 93 and applied with R-wave signal 27, heart rate signal 23, and current cuff pressure ($P_i$) to block 130, which determines the opening and closing times of cardiac gates 26 as +/− tolerances from centroid 112. We have found that Korotkoff sounds generally occur relatively later in the gate when systolic pressure is being measured, and progressively occur earlier in the gate as the blood pressure approaches diastolic. Moreover, the timing of the Korotkoff sounds during the gate is a function of heart rate. Thus, rather than setting cardiac gate 26 symmetrically with respect to centroid 105, block 130 adaptively adjusts the opening/closing times of gate 26 during the measurement cycle in accordance with blood pressure and heart rate, as will now be described.

Figure 6:
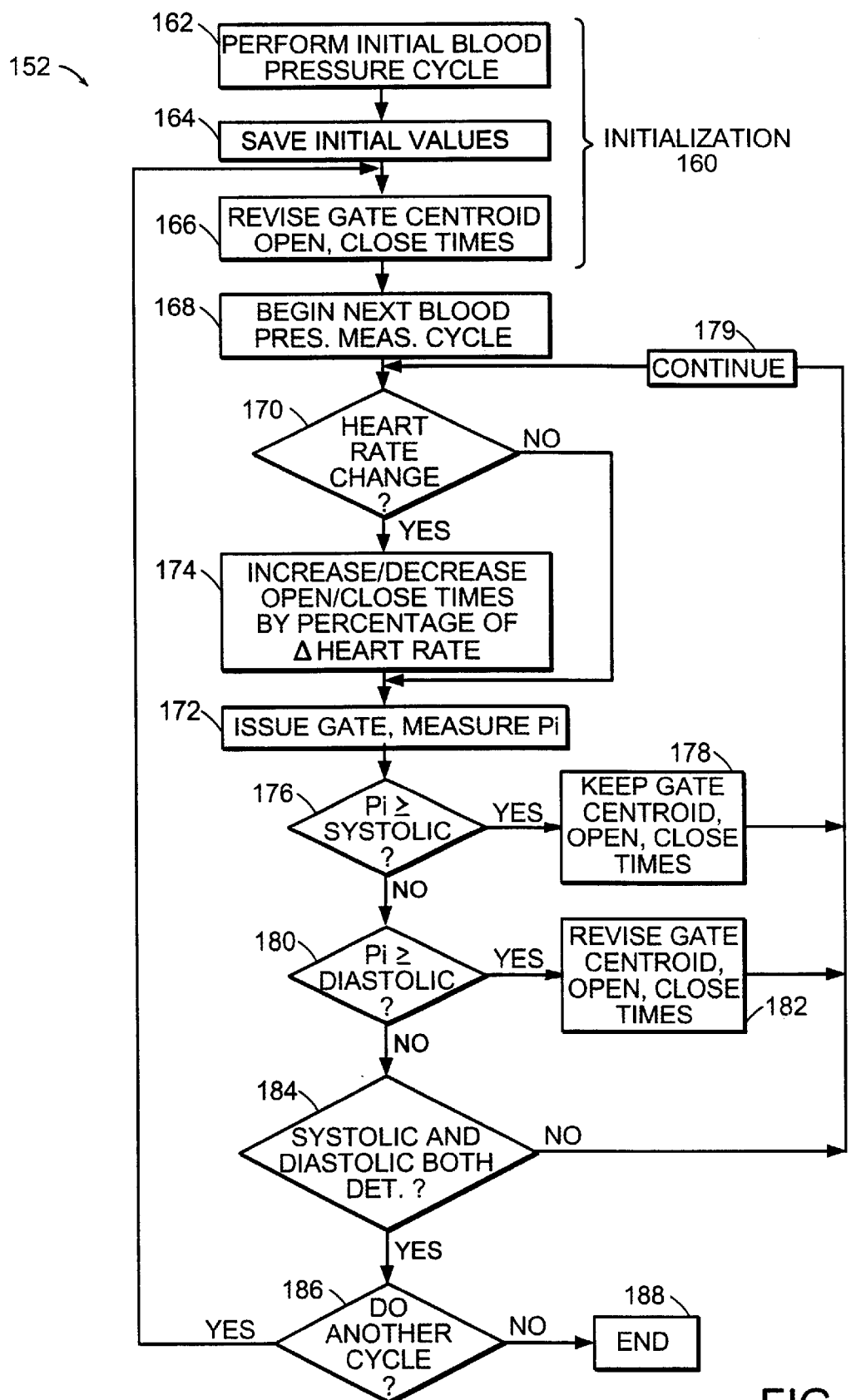
FIG. 6 is a flow chart that shows adaptively adjusting the timing and duration of the cardiac gate signals during operation.

Referring also to FIG. 6, pressure compute process 30 executes a procedure 152 for establishing the timing and duration of cardiac gates 26 (based on the centroid determination discussed above) for each blood pressure measurement cycle. Procedure 152 also adaptively changes the gate opening and closing times during the cycle in accordance with changes in cuff pressure (i.e., as the cuff pressure is progressively decreased during the measurement cycle) and changes in heart rate. As a result, cardiac gates 26 are issued at times, and for durations, that most likely coincide with the occurrence of valid Korotkoff sounds, thereby further increasing the noise immunity of blood pressure monitor 10.

Procedure 152 is as follows. First, blood pressure monitor 10 is initialized (step 160) by performing the initial measurement discussed above with the patient at rest (step 162). Because monitor 10 has not yet gathered blood pressure and heart rate data on the patient, the cardiac gates for the initial measurement are not determined based on the centroid calculation described above. Instead, during the initial measurement cycle, cardiac gates 26 are issued immediately upon the detection of R-wave signal 27 and have a duration set at 50% of the value of the heart period represented by the rate stored in memory location 97 (the heart rate is measured by circuit 100, FIG. 5, as discussed above). Because the patient is at rest, noise should be at a minimum, and the wide gates help ensure that valid Korotkoff sounds are not missed.

During the initial measurement cycle, cuff 16 is fully inflated and then incrementally deflated after each R-wave. History thresholds 76a, 76b for the initial cycle are set as described above. Cuff pressures $P_i$, K-sound data (i.e., peak $K_D$ and time $K_D$) and scores from each channel 60a, 60b, and centroids ($C_i$) are stored in memory table 94 (FIG. 4) as described above. The initial systolic and diastolic pressures are computed from the scores in the manner discussed above.

The initial systolic and diastolic pressures are saved (step 164) in memory locations 96, 98, respectively (FIG. 3). Other initial values are saved in step 164 as well. They include the predicted systolic pressure (location 87), the final centroid ($C_n$) determined during the initial cycle (location 93), the most recent heart rate (location 97), and the average diastolic pressure (location 99). The four highest amplitude real-time peak $K_D$ signals obtained during the initial blood pressure measurement cycle having scores of 75 or 100 are also used to revise the average maximum $K_D$ value 80 (FIG. 3), and the history thresholds 76a, 76b and the reference level for channel selection block 92 (stored in buffer 91) are revised accordingly, as discussed above.

At the start of the next blood pressure measurement cycle (which we will term the "current measurement cycle"), pressure compute process 30 retrieves the initial value for the cardiac gate centroid, and sets the initial cardiac gate opening and closing times for the current measurement cycle based on the centroid (step 166). The current blood pressure measurement cycle then begins (step 168), commencing at cuff pressures above the initial systolic pressure (stored in memory location 96). Process 30 determines whether the heart rate has changed with respect to the most recent heart rate stored in memory location 97 (step 170). If the heart rate has not changed, process 30 issues a cardiac gate 26 (step 172) with opening and closing at times designated in step 166.

If the heart rate has changed, process 30 revises the gate opening and closing times by a percentage of the change in heart period (step 174). If the heart rate is below 100 beats per minute, this fraction is 25%; otherwise, the times are adjusted by only 8% of the change in heart period. Different percentages are used because the R-wave to Korotkoff sound interval does not change linearly with variations in heart rate. The direction of the adjustments corresponds to the direction (an increase or decrease) in which the heart period changed. (This technique is also used to adjust the cardiac gate opening and closing times during the initial blood pressure measurement cycle, step 162.)

A measurement of pressure $P_i$ is taken for each issued cardiac gate 26, and the signals produced by transducers 18, 20 during gate 26 are analyzed for the presence of Korotkoff sounds or noise in the manner described above (step 172). Each time that cuff 16 is incrementally deflated, pressure compute process 30 determines whether the opening and closing times of the next cardiac gate 26 should be changed in accordance with the current pressure of cuff 16. If the current pressure $P_i$ of cuff 16 is greater than or equal to the most recently measured systolic pressure, as saved in location 96 (step 176), the gate centroid and opening/closing times are maintained at the times set in either step 166 or step 174 (step 178). The blood pressure measurement cycle then continues (step 179) by proceeding back to step 170.

If the current blood pressure measurement cycle has proceeded sufficiently so that cuff pressure $P_i$ is between the most recent diastolic pressure and the most recently measured diastolic pressure stored in location 98 (step 180), the opening and closing times for subsequent cardiac gates are adjusted accordingly (step 182). In particular, Korotkoff sounds typically occur progressively sooner after the R-wave as cuff pressure decreases. This effect is reflected in the timing of centroids $C_i$ stored in table 94, which tend to occur with shorter delays from R-wave signals 27 with decreasing cuff pressures $P_i$. Thus, when the cuff pressure is less than systolic pressure (step 180), process 30 recalculates the centroid for the next cardiac gate 26 using the most-recently stored centroid value $(C_i)$ in table 94 (step 182). Process 30 also sets the opening and closing times for the next gate 26 based on the new centroid in step 182. Thereafter, the blood pressure measurement cycle continues (step 179) by proceeding back to step 170. This process is repeated for each heartbeat in which the associated pressure exceeds diastolic.

When both systolic and diastolic pressures have been measured (step 184), the current blood pressure measurement cycle is complete. Process 30 updates the systolic and diastolic pressure values and the heart rate value stored in memory locations 87 and 96–99. If another blood pressure measurement cycle is to be performed (step 186), the procedure returns to step 166. If no further measurement cycles are to be performed, the procedure ends (step 188).

At the start of the next measurement cycle (steps 166, 168), pressure compute process 30 replaces the cardiac gate centroid stored in location 93 with the last centroid $(C_n)$ calculated and stored in table 94 (FIG. 4) in the previous measurement cycle. Process 30 determines the initial cardiac gate opening and closing times are based on the heart rate stored in memory location 97. In addition, the average maximum $K_D$ level and history thresholds 76a, 76b are revised by blocks 80, 82 (FIG. 3). Process 30 then clears table 94, and the new measurement cycle then proceeds in the same manner as discussed above.

Before process 30 clears table 94, it may re-evaluate the K-sound data and scores from the previous measurement cycle in view of the updated history thresholds to determine whether the systolic and diastolic measurements should be revised. Process 30 does this by rescoring the peak $K_D$ signals (from both channels 60a, 60b) using updated history thresholds (along with the other data used in the scoring procedure, which as discussed above is also stored on a heartbeat-by-heartbeat basis in table 94). In addition, the updated history threshold is revised in accordance with the non-gated $K_D$ signals stored in table 94 so that process 30 can determine whether to use scores derived from real-time channel 60a or accumulate channel 60b in the analysis. If the re-evaluation yields different values for systolic and/or diastolic blood pressure, the new values are displayed (54) and printed, and are used to recalculate the blood pressure values stored in memory locations 87 and 96, 98, and 99 (FIG. 4). The re-evaluation is particularly useful for the data obtained during the initial measurement cycle, when the thresholds are intentionally set quite low.

Other embodiments are within the scope of the following claims.

For example, accumulators 65 (FIG. 2) need not be synchronized with the QRS complex (i.e., the R-wave). The timing for accumulators 65 may be provided by any signal (internal to or external from the patient) that is synchronized with the cardiac cycle. SCLK can be any suitable frequency that satisfies the Nyquist requirement.

Other features of the '781 patent that are not discussed herein (such as large amplitude noise suspension, adjustment of the thresholds for noisy environments, and the use of separate noise sensors) may be used. The alternative approaches to measuring blood pressure discussed in the '781 patent may also be used with the present invention.

Accumulation channel 60b (FIG. 2) may accumulate the transducer signals over a different number of heart periods. Increasing the number of periods will increase the signal-to-noise ratio still further, but will also introduce more delay in detecting valid Korotkoff sounds. Thus, the measurement of systolic and diastolic pressures will also be delayed somewhat.

Other types of transducers may be used. A single transducer may be used in place of two transducers.

What is claimed is:

1. A method for use in measuring blood pressure, comprising
    detecting mixed signals during time periods, the mixed signals including biological signals indicative of blood pressure and noise signals not indicative of blood pressure,
    evaluating the mixed signals over a plurality of the time periods to aid in discriminating the biological signals from the noise signals,
        the evaluating comprising assembling the mixed signals detected at corresponding times during the plurality and analyzing the assembled mixed signals to aid in discriminating the biological signals from the noise signals, the analyzing comprising developing a candidate blood pressure signal based on the biological signals indicative of blood pressure in the assembled mixed signals, and determining whether the candidate blood pressure signal should be used to measure blood pressure, the determining comprising determining whether the candidate blood pressure signal should be used to measure blood pressure based on whether it exceeds a plurality of combinations of different thresholds, and assigning a score to the candidate blood pressure signal that indicates a likelihood that the candidate blood pressure signal is valid blood pressure signal, the score being based on which thresholds are exceeded.

2. The method of claim 1 wherein the assembling includes accumulating the mixed signals detected at the corresponding times during the plurality of time periods.

3. The method of claim 1 wherein the time periods are cardiac cycle intervals.

4. The method of claim 3 wherein the assembling includes accumulating samples of the mixed signals that are taken at corresponding time delays after a start of each of the cardiac cycle intervals.

5. The method of claim 4 further comprising detecting the start of each cardiac cycle interval based on an occurrence of a timing signal that is synchronous with the cardiac cycle.

6. The method of claim 5 wherein the timing signal is an R-wave signal.

7. The method of claim 1 wherein the determining comprises determining that the candidate blood pressure signal should be used to measure blood pressure if it exceeds a threshold.

8. The method of claim 1 further comprising measuring blood pressure based on the scores of the candidate blood pressure signals.

9. The method of claim 1 wherein the plurality of thresholds include a history threshold, and further comprising developing the history threshold based on previously detected biological signals indicative of blood pressure in the assembled mixed signals that have exceeded the threshold.

10. The method of claim 1 wherein the plurality of thresholds include a noise threshold, and further comprising developing the noise threshold based on the noise signals not indicative of blood pressure in the assembled mixed signals.

11. The method of claim 1 further comprising developing the candidate blood pressure signal from the biological signals indicative of blood pressure in the assembled mixed signals only during a selected portion of one of the time periods.

12. The method of claim 11 wherein the time periods are cardiac cycle intervals, and further comprising determining the selected portion based on levels of the biological signals indicative of blood pressure in the assembled mixed signals and times during the cardiac cycle intervals during which they are detected.

13. The method of claim 1 wherein the detecting includes detecting the mixed signals with a plurality of transducers on a blood pressure cuff, and further comprising assembling the mixed signals detected at corresponding times during the plurality of time periods by each of the transducers, and analyzing the assembled mixed signals to aid in discriminating the biological signals from the noise signals.

14. The method of claim 13 further comprising combining the assembled mixed signals from each of the transducers with each other to develop a candidate blood pressure signal in which the biological signals are reinforced and the noise signals are attenuated.

15. The method of claim 14 wherein the combining includes subtracting the assembled mixed signals detected by one of the transducers from the assembled mixed signals detected by another one of the transducers.

16. The method of claim 14 further comprising determining whether the candidate blood pressure signal should be used to measure blood pressure based on whether it exceeds a plurality of combinations of different thresholds.

17. The method of claim 16 further comprising assigning a score to the candidate blood pressure signal that indicates a likelihood that the candidate blood pressure signal is a valid blood pressure signal, the score being based on which thresholds are exceeded.

18. The method of claim 16 further comprising measuring blood pressure based on the scores of the candidate blood pressure signals.

19. The method of claim 16 wherein one of the plurality of thresholds includes a history threshold, and further comprising developing the history threshold based on previously determined candidate blood pressure signals.

20. The method of claim 16 wherein one of the thresholds includes a noise threshold, and further comprising developing the noise threshold based on the noise signals detected during the time periods.

21. The method of claim 20 further comprising developing the noise threshold by combining the assembled mixed signals from the plurality of transducers so as to reinforce the noise signals and attenuate the biological signals.

22. The method of claim 21 wherein the combining to develop the noise threshold includes summing the assembled mixed signals from the plurality of transducers.

23. Apparatus for use in a blood pressure measuring device, comprising at least one transducer for detecting mixed signals during time periods, the mixed signals including biological signals indicative of blood pressure and noise signals not indicative of blood pressure, and processing circuitry for evaluating the mixed signals over a plurality of the time periods to aid in discriminating the biological signals from the noise signals, the processing circuitry being adapted to:

develop a candidate blood pressure signal from the biological signals indicative of blood pressure in the assembled mixed signals, and determine whether the candidate blood pressure signal should be used to measure blood pressure, determine whether the candidate blood pressure signal should be used to measure blood pressure based on whether it exceeds a plurality of different thresholds, and assign a score to the candidate blood pressure signal that indicates a likelihood that the candidate blood pressure signal is a valid blood pressure signal, the score being based on which thresholds are exceeded.

24. The apparatus of claim 23 wherein the processing circuitry comprises circuitry for assembling the mixed signals detected at corresponding times during the plurality of time periods, and a processor for analyzing the assembled mixed signals to aid in discriminating the biological signals from the noise signals.

25. The apparatus of claim 24 wherein the circuitry for assembling includes an accumulator for accumulating the mixed signals detected at the corresponding times during the plurality of time periods.

26. The apparatus of claim 25 wherein the apparatus includes a plurality of transducers each of which detects the mixed signals during the time periods, and further comprising an accumulator associated with each of the transducers for accumulating the mixed signals detected thereby at the corresponding times during the plurality of time periods, the processor analyzing the accumulated mixed signals from the accumulators to aid in discriminating the biological signals from the noise signals.

27. The apparatus of claim 24 wherein the time periods are cardiac cycle intervals.

28. The apparatus of claim 27 wherein the accumulator is controlled to accumulate samples of the mixed signals that are taken at corresponding time delays after a start of each of the cardiac cycle intervals.

29. The apparatus of claim 28 further comprising circuitry for detecting the start of each cardiac cycle interval based on an occurrence of a timing signal that is synchronous with the cardiac cycle.

30. The apparatus of claim 29 wherein the timing signal is an R-wave signal.

31. The apparatus of claim 23 wherein the processing circuitry is further adapted to determine that the candidate blood pressure signal should be used to measure blood pressure if it exceeds the threshold.

32. The apparatus of claim 23 wherein the processing circuitry is adapted to measure blood pressure based on the scores of the candidate blood pressure signals.

33. The apparatus of claim 23 wherein the plurality of thresholds include a history threshold, the processing circuitry being adapted to develop the history threshold based on previously detected biological signals indicative of blood pressure in the assembled mixed signals that have exceeded the threshold.

34. The apparatus of claim 23 wherein the plurality of thresholds include a noise threshold, the processing circuitry being adapted to develop the noise threshold based on the noise signals not indicative of blood pressure in the assembled mixed signals.

35. The apparatus of claim 23 wherein the processing circuitry is adapted to develop the candidate blood pressure signal from the biological signals indicative of blood pressure in the assembled mixed signals only during a selected portion of one of the time periods.

36. The apparatus of claim 35 wherein the time periods are cardiac cycle intervals, the processing circuitry being adapted to determine the selected portion based on levels of the biological signals indicative of blood pressure in the assembled mixed signals and times during the cardiac cycle intervals during which they are detected.

37. A method for use in measuring blood pressure, comprising detecting mixed signals that include biological signals indicative of blood pressure and noise signals not indicative of blood pressure, determining if a noise level exceeds a threshold, and analyzing the mixed signals in a first way if the noise level does not exceed the threshold to discriminate the biological signals from the noise signals, and analyzing the mixed signals in a second, different way if the noise level exceeds the threshold to discriminate the biological signals from the noise signals, the detecting including detecting the mixed signals during time periods, the first way of analyzing comprising evaluating the mixed signals in each of the time periods individually, and the second way of analyzing comprising evaluating the mixed signals over a plurality of the time periods.

38. A method for use in measuring blood pressure, comprising detecting mixed signals that include biological signals indicative of blood pressure and noise signals not indicative of blood pressure, determining if a noise level exceeds a threshold, and analyzing the mixed signals in a first way if the noise level does not exceed the threshold to discriminate the biological signals from the noise signals, and analyzing the mixed signals in a second, different way if the noise level exceeds the threshold to discriminate the biological signals from the noise signals, the detecting including detecting the mixed signals during time periods, the second way of analyzing comprising assembling the mixed signals detected at corresponding times during the time periods, and analyzing the assembled mixed signals to discriminate the biological signals from the noise signals.

39. The method of claim 38 wherein the time periods are cardiac cycle intervals and the assembling includes accumulating samples of the mixed signals that are taken at corresponding time delays after a start of each of the cardiac cycle intervals.

40. The method of claim 37 or 38 wherein the determining is based on the detected noise signals not indicative of blood pressure in the mixed signals.

41. The method of claim 37 or 38 further comprising performing the analyzing on the mixed signals detected during cardiac cycle intervals, and performing the determining based on the mixed signals received outside of the cardiac cycle intervals.

42. A method for use in measuring blood pressure, comprising detecting mixed signals which include biological signals indicative of blood pressure and noise signals indicative of blood pressure, developing a candidate blood pressure signal based on the biological signals indicative of blood pressure in the mixed signals, determining whether the candidate blood pressure signal should be used to measure blood pressure based on whether it exceeds a plurality of combinations of different thresholds, and assigning a score to the candidate blood pressure signal that indicates a likelihood that the candidate blood pressure signal is a valid blood pressure signal, the score being based on which thresholds are exceeded.

43. The method of claim 42 further comprising measuring blood pressure based on the scores of the candidate blood pressure signals.

44. The method of claim 42 wherein the plurality of thresholds include a history threshold, and further comprising developing the history threshold based on previously detected biological signals indicative of blood pressure in the mixed signals that have exceeded the threshold.

45. The method of claim 42 wherein the plurality of thresholds include a noise threshold, and further comprising developing the noise threshold based on the noise signals not indicative of blood pressure in the mixed signals.

46. A method for use in measuring blood pressure, comprising detecting mixed signals during time periods, the mixed signals including biological signals indicative of blood pressure and noise signals not indicative of blood pressure, selecting a portion of the time periods based on levels of the biological signals indicative of blood pressure in the mixed signals and times during a cardiac cycle intervals during which they are detected, the selecting comprising designating a nominal time from initiation of a cardiac cycle interval based on a weighted average of times during the cardiac cycle at which the biological signals indicative of blood pressure are detected and levels of said biological signals, starting the portion of the time period at a first time prior to the nominal time, and ending the portion of the time period at a second time after the nominal time, and analyzing the biological signals indicative of blood pressure in the mixed signals only during the selected portion of the time periods to develop a candidate blood pressure signal.

47. The method of claim 46 further comprising selecting the nominal time differently according to whether systolic or diastolic pressure is being measured.

48. The method of claim 46 further comprising changing the first time and the second time in accordance with changes in heart rate.

49. The method of claim 46 further comprising determining whether the candidate blood pressure signal should be used to measure blood pressure based on the analyzing of the biological signals indicative of blood pressure in the mixed signals during the selected portion of the time periods.

* * * * *

UNITED STATES PATENT AND TRADEMARK OFFICE
CERTIFICATE OF CORRECTION

PATENT NO.    : 6,258,037 B1
DATED         : July 10, 2001
INVENTOR(S)   : Mr. Neal B. Dowling Jr.

Page 1 of 1

It is certified that error appears in the above-identified patent and that said Letters Patent is hereby corrected as shown below:

Column 11,
Line 43, replace "$K_D$)" with -- $K_D$). --.

Column 12,
Line 39, after "thresholds." start a new paragraph.
Line 57, replace "9" with -- 90 --.

Column 17,
Line 59, replace "with" with -- ith --.

Column 18,
Line 54, replace "$K_D$" with -- $\overline{K}_D$ --

Column 20, claim 1,
Line 67, before "and" nsert -- of time periods --.

Column 24, claim 42,
Line 41, after "signals" insert -- not --.

Signed and Sealed this

Fourth Day of December, 2001

*Attest:*

NICHOLAS P. GODICI
*Attesting Officer*     *Acting Director of the United States Patent and Trademark Office*